United States Patent [19]
Utterberg

[11] Patent Number: 5,951,519
[45] Date of Patent: Sep. 14, 1999

[54] ASEPTIC FEMALE CONNECTOR

[75] Inventor: David S. Utterberg, Seattle, Wash.

[73] Assignee: DSU Medical Corporation, Las Vegas, Nev.

[21] Appl. No.: 08/840,712

[22] Filed: Apr. 25, 1997

[51] Int. Cl.⁶ ................................................. A61M 5/178
[52] U.S. Cl. .......................................... 604/167; 604/256
[58] Field of Search ............................ 604/34, 167, 250, 604/256, 265, 283, 905; 606/157, 158

[56] References Cited

U.S. PATENT DOCUMENTS

| | | | |
|---|---|---|---|
| 3,741,217 | 6/1973 | Ciarco | 604/283 |
| 4,429,852 | 2/1984 | Tersteegen et al. | |
| 4,802,650 | 2/1989 | Stricker | 604/250 |
| 5,190,534 | 3/1993 | Kendell | 604/905 |
| 5,385,372 | 1/1995 | Utterberg | |
| 5,413,561 | 5/1995 | Fischell et al. | 604/167 |
| 5,569,206 | 10/1996 | Gorman, Jr. et al. | 604/167 |
| 5,674,209 | 10/1997 | Yarger | 604/256 |

FOREIGN PATENT DOCUMENTS

WO97/22535  6/1997  WIPO.

*Primary Examiner*—Michael Buiz
*Assistant Examiner*—Julian W. Woo
*Attorney, Agent, or Firm*—Gerstman, Ellis & McMillin, Ltd.

[57] ABSTRACT

A female tube connector defining a tapered socket having an open, inner end communicating with the lumen of a tube, and a sealing cap proportioned to close the connector and to seal the tapered socket. The sealing cap comprises a cap body and a tapered projection proportioned to sealingly fit within the tapered socket. The projection is carried by the cap body and extends beyond the cap body by a distance to permit the projection to substantially completely occupy the whole length of the tapered socket when the cap is closing the female connector. The projection has an outer surface that carries an antiseptic material, so that upon such closure the interior of the tube connector can be sterilized between uses.

24 Claims, 1 Drawing Sheet

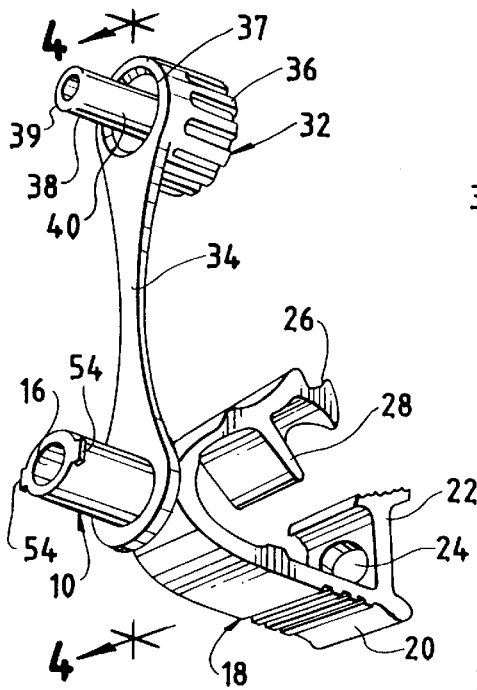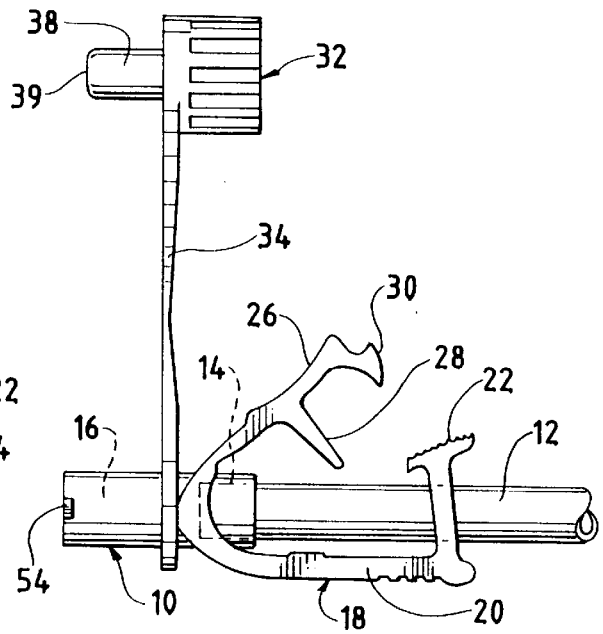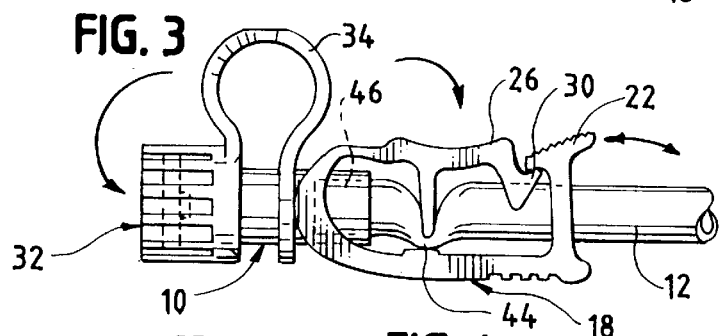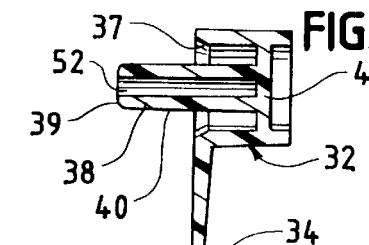

ASEPTIC FEMALE CONNECTOR

BACKGROUND OF THE INVENTION

Male and female tube connectors such as luer connectors are commonly used in blood and medical solution handling, as well as in many other uses. Specifically, such connectors are commonly used in commercially available hemodialysis sets and other blood handling sets as access ports for medicament infusion or sampling.

Typically, such connectors respectively comprise a tapered socket and a tapered projection that together form a conical surface seal and connection.

Caps are commonly used for female luer connectors, which caps may define a threaded skirt for engaging a pair of "ears" projecting outwardly from the female connector, while a tapered, projecting portion of the cap extends into the conical bore of the luer connector. By the ISO standards, which are industry standards that govern the design of commercial medical products, the tapered projection of said caps only extends for a total length of about 7.5 mm., and about 2.1 mm. beyond the skirt of the cap. The ISO dimensions of male and female luer engagement leave a portion of the tapered socket of the female tube connector open, thus defining a free space in the female connector while the cap is sealing the end of the female connector.

Such female connectors are placed on tube ends, such as the ends of branching lines extending outwardly from various blood sets including hemodialysis sets. Such branching lines may be used to connect to a source of parenteral solution, a source of heparin solution, or a pressure monitor, for example. Other access ports comprise the well-known elastomeric injection sites which are accessed with a needle.

Prior to initial removal of the cap, the female connector is sterile, being in its as-manufactured condition. However, after removal of the cap and use of the connector, the cap can be replaced again, but the female connector, and the lumen of the connected tubing, are no longer sterile. Despite this fact, at the present time no attempts are generally made in clinical use to disinfect the female connectors. It is thought to be impractical to sterilize the internal surfaces of the female connector sockets, and it is even more difficult to sterilize adjacent lengths of the tube interiors which connect with the female connectors.

Another type of tube connection is provided by needle injection sites. The outer surfaces of such injection sites are typically disinfected prior to every use. However, such disinfection is relatively ineffective because the antiseptic is swabbed on only a few seconds prior to puncture with a needle.

Thus there is a need for a tube connector which can be more reliably sterilized between uses.

By this invention, a closure cap for a female tube connector type of access port is provided in which internal sterilization or other antimicrobial effect can take place in a more reliable, easy manner. By this invention, a female tube connector, and a length of the tubing adjacent thereto, can be effectively resterilized between uses, to provide further improvement in the aseptic practice of blood handling, parenteral solution administration, or the like.

DESCRIPTION OF THE INVENTION

In accordance with this invention there is provided a female tube connector defining a typically tapered socket and having an open, inner end communicating with the lumen of a tube, as is conventional in the prior art. A sealing cap is provided, the cap being proportioned to close the connector and to seal the tapered socket.

The sealing cap comprises a cap body and a typically tapered projection proportioned to sealingly fit within the tapered socket of the tube connector. The projection is carried by the cap body, and extends by a distance to permit the projection to substantially occupy the whole length of the tapered socket when the cap is closing the female connector, contrary to conventional commercial practice. Preferably, the projection extends beyond the cap body by a distance of at least about 4 mm. allowing the projection to be wiped with, or dipped into, antiseptic solution.

Thus, the projection preferably has an outer surface that carries an antiseptic material, typically a volatile antiseptic material such as povidone iodine or alcohol. When the cap closes onto the connector, essentially the complete, tapered socket of the connector is in engagement with the outer surface of the tapered projection and in contact with antiseptic, for improved internal surface sterilization. Also, a small portion of antiseptic is pushed inwardly to provide vapor for antimicrobial action in the interior of the adjacent tube and rear portions of the connector. Since the cap will typically remain in position for a period of minutes or more prior to reuse, an adequate dwell time can be provided for the antiseptic to exhibit excellent effect.

Alternatively, other antiseptics may be used if and as desired, such as antiseptics that are bonded to the tapered surface of the projection, for example a thin silver coating or other antimicrobial agent.

Preferably, the tapered projection of the cap comprises a closed-end, hollow tube, with the closed end being the end which faces away from the female connector when the cap is applied, and with the other, outer end of the hollow tube of the tapered projection being open. Thus, the tapered projection has an increase in flexibility, and is more capable of flexing and yielding if it is too long by a matter of thousandths of an inch for the tapered socket, and is abutting against a surface such as the end of the plastic tube upon which the female connector may be carried. Because of this increased softness and flexibility caused by making the projection of the cap open-ended, the system is more tolerant of dimensional error in manufacturing.

Also, if desired, the lumen of the tubular, tapered projection may contain an antiseptic which may diffuse through the walls of the projection, or diffuse out of the open end thereof, to provide an automatic source of antiseptic to the system, so that antiseptic does not have to be manually applied prior to placing the cap into position.

Typically, a flexible connection such as a tether may connect the cap and the connector, so that the cap is not lost and can always be adjacent to the connector for opening and closing as may be desired. Particularly, the hinged connection system between a cap and a connector as defined in Utterberg U.S. Pat. No. 5,385,372 may be used, the disclosures of which are incorporated by reference herein.

Also, it is preferred for the female connector of this invention to carry a tube clamp to selectively seal and to open the tube which carries the female connector at a flexible portion of the tube adjacent to such connector. Squeeze-type tube clamps of many different designs are known. Such a clamp may be integrally co-molded with the connector to provide a single, integral piece, if desired.

An advantage of this lies in the fact that the clamping of the tube takes place adjacent to the female connector. Thus, after such sealing with the clamp, the internal volume defined by the closed clamp and a small length of the tubing is both small and quantitatively defined. That entire sealed area will be exposed to a volatile antiseptic (if such is used) for a length of time between the closing of the connector and its next reopening for subsequent use. Such a dwell time of minutes or hours can be adequate for a relatively small amount of antiseptic to have highly effective antimicrobial effect on the enclosed internal area of the connector and a small portion of the tubing interior between the cap and the squeeze clamp carried by the female connector in preferred embodiments of this invention. This antisepsis provides not only an improvement on the use of prior art female luer access ports and caps, but also provides an improvement on the use of known needle injection site access ports.

DESCRIPTION OF THE DRAWINGS

In the drawings, FIG. 1 is a perspective view of a female luer connector and an attached sealing cap in accordance with this invention;

FIG. 2 is an elevational view of the tube connector and cap of FIG. 1, shown to be attached to the end of a length of plastic tubing of a blood set for hemodialysis;

FIG. 3 is an elevational view of the connector and cap of FIG. 2, shown in the closed configuration; and FIG. 4 is a longitudinal sectional view of the cap shown in FIGS. 1–3.

DESCRIPTION OF SPECIFIC EMBODIMENTS

Referring to the drawings, FIG. 1 shows a female luer connector 10 of generally conventional design except as otherwise shown herein, having a conically tapered socket 16.

Luer connector 10 connects with conventional flexible tubing 12 as shown in FIG. 2, for example branch tubing extending out from the main tubing of an arterial or a venous set for hemodialysis. Alternatively, female luer 10 may connect one of the main ends of such a hemodialysis set or other blood handling set. Tubing 12 may be sealed into bore 14 of connector 10, which is typically cylindrical and not tapered.

Female connector 10 as shown is integrally molded with and connected to a pressure clamp 18, which comprises a clamp body 20, an upstanding tube guide and first latch 22, having an aperture 24 through which tubing 12 extends, and a pivotable clamp pressure member 26, having a downwardly extending projection 28 to close off the lumen of tube 12 when the clamp is in closed position as shown in FIG. 3. Pressure member 26 also carries a second latch 30 to latch with the first latch 22 as also shown in FIG. 3. Thus, the user can open or close flow through tubing 12 by the integral pressure clamp 18 carried by female connector 10. First latch 22 may be manually pivoted out of engagement with second latch 30, to open the clamp again.

Luer connector 10 may also be integrally co-molded with a closure cap 32 and a flexible tether or arm 34. Alternatively, cap 32 and tether 34 may be added as a separate part. Cap 32 is tethered in adjacent relation with female luer connector 10, being capable of entering into closing relation therewith as shown in FIG. 3.

Cap 32 comprises a cap body 36, and a tapered projection 38, which is proportioned to sealingly fit within tapered socket 16.

In accordance with this invention, projection 38 extends beyond the cap body 36 and the skirt 37 defined thereby, generally by at least about 4 mm. and typically 7–10 mm., to permit projection 38 to substantially completely occupy the whole length of tapered socket 16 of female connector 10 when cap 32 is closing the female connector. Tapered projection 38 may have an outer surface 40 which is coated with an antiseptic, for example by coating with a volatile antiseptic such as povidone iodine or alcohol immediately prior to closure. Projection 38 then extends substantially the entire length of tapered bore 16 in the closed configuration, extending for example to tapered bore end 42 in FIG. 4, up to bore 14 which carries tubing 12. The antiseptic is thus pressed against substantially the entire surface of bore 16, while vapors will spread and be retained by the closed cap 32 at one end of female connector 10. At the other end of the female connector 10, clamp 18 can be closed to seal tubing 12 at position 44, resulting in a small, enclosed lumen space 46 between position 44 and the inner end of projection 38 (at or near line 42). This inner volume 46 is small, and of a generally predictable volume for each specific system designed in accordance with this invention. Antiseptic vapors will migrate from tapered projection 38 into this small volume to provide sterilization of the surfaces exposed within volume 46 after exposure of a few minutes to the antiseptic vapors.

Thus, the connector of this invention can be used to resterilize female connectors after they have been used, for a significant improvement in the aseptic procedure of blood handling, whereas in the prior art, the interiors of female connectors are rarely sterilized between initial use and reuse.

Preferably, tapered projection 38 is a tube, closed at its inner end 48 within cap body 36 which faces away from connector 10 when the cap 32 is applied, and open at its outer end 39 which extends beyond cap body 36. The resulting lumen 52 of hollow projection 38 may be filled with antiseptic if desired to provide a continuing sterilization effect to the sealed interior 46.

It is also preferred for tapered projection 38 to extend at least about 4 mm., and typically at least 5 mm., outwardly beyond skirt 37 of the cap body, as shown. In the prior art, such a tapered sealing projection of luer caps projects outwardly only about 2.1 mm. beyond the skirt, in accordance with the ISO standards.

The strap or tether 34 may be a flexible strap of conventional design. If strap 34 is pivotally attached to female connector 10 or to cap 32, then skirt 37 of cap 32 can be threaded to engage the ears or projections 54 of female connector 10 in conventional manner. If strap 34 is integrally molded with connector 10 and clamp 18, then cap 32 will not have threads, and will connect to connector 10 with a friction fit in normal circumstances.

The above has been offered for illustrative purposes only, and is not intended to limit the scope of the invention of this application, which is as defined in the claims below.

That which is claimed:

1. A female tube connector defining a tapered socket having an open inner end communicating with the lumen of a tube, and a sealing cap proportioned to close said connector and to seal said tapered socket, said sealing cap comprising a cap body and a tapered projection proportioned to sealingly fit within said tapered socket with a luer mating seal, said projection being carried by said cap body and extending beyond said cap, body by a distance to permit said projection to substantially completely occupy and seal the whole length of said tapered socket when said cap is closing said female connector, said projection having an outer surface that carries an antiseptic material.

2. A connector and cap of claim 1 in which said tapered projection comprises a hollow tube having an closed inner end.

3. The connector and cap of claim 2 in which said tapered projection defines a lumen, open at the projection end which extends beyond said cap body.

4. The connector and cap of claim 2 in which said tapered projection defines a lumen which contains an antiseptic.

5. The connector and cap of claim 1 in which said cap is flexibly connected to said connector.

6. The connector and cap of claim 1 in which said connector carries a tube clamp to selectively seal and open said tube at a flexible portion of said tube adjacent to said connector.

7. The connector and cap of claim 1 in which said tapered projection extends at least about 4 mm. outwardly beyond said cap body.

8. A female tube connector defining a tapered socket having an open inner end communicating with the lumen of a tubes and a sealing cap proportioned to close said connector and to seal said tapered socket, said sealing cap comprising a cap body and a tapered projection proportioned to sealingly fit within said tapered socket with a luer mating seal, said projection being carried by said cap body and extending beyond said cap body by a distance to permit said projection to substantially completely occupy the whole length of said tapered socket when said cap is closing said female connector, said tapered projection comprising a hollow tube having an impenetrably closed inner end, and having an outer surface that carries an antiseptic material.

9. The connector and cap of claim 8 in which said tapered projection defines a lumen, open at the projection end which extends beyond said cap body.

10. The connector and cap of claim 8 in which said cap is flexibly connected to said connector.

11. The connector and cap of claim 8 in which said connector carries a tube clamp to selectively seal and open said tube at a flexible portion of said tube adjacent to said connector.

12. The connector and cap of claim 8 in which said tapered projection extends at least about 4 mm. outwardly beyond said cap body.

13. The connector and clamp of claim 12 in which said connector carries a tube clamp to selectively seal and open said tube at a flexible portion of said tube adjacent to said connector.

14. The connector and cap of claim 13 in which said cap is flexibly connected to said connector.

15. The connector and cap of claim 14 in which said tapered projection defines a lumen, open at the projection end which extends beyond said cap body.

16. The connector and cap of claim 15 in which said lumen contains an antiseptic.

17. A female tube connector defining a tapered socket having an open inner end communicating with the lumen of a tube, and a sealing cap proportioned to close said connector and to seal said tapered socket, said sealing cap comprising a cap body and a tapered projection proportioned to sealingly fit within said tapered socket, said projection being carried by said cap body and extending beyond said cap body by a distance to permit said projection to substantially completely occupy the whole length of said tapered socket when said cap is closing said female connector, and further in which said connector carries a tube clamp to selectively seal and open said tube at a flexible portion of said tube adjacent to said connector.

18. The connector and cap of claim 17 in which said tapered projection extends at least about 4 mm. outwardly beyond said cap body.

19. The connector and cap of claim 17 in which said tapered projection has an outer surface that carries an antiseptic material, said tapered projection being proportioned to sealingly fit within said tapered socket with a luer mating seal.

20. The connector and cap of claim 17 in which said tapered projection comprises a hollow tube having an impenetrably closed inner end and a lumen, open at the projection end which extends beyond said cap body.

21. The connector and cap of claim 20 in which said lumen contain an antiseptic.

22. A blood handling set which comprises flexible tubing, the flexible tubing having an end carrying a female tube connector and sealing cap of claim 1.

23. A blood handling set which comprises flexible tubing, the flexible tubing having an end carrying a female tube connector and sealing cap of claim 8.

24. A blood handling set which comprises flexible tubing, the flexible tubing having an end carrying a female tube connector and cap of claim 17.

\* \* \* \* \*